(12) United States Patent
Vastola (10) Patent No.: US 9,392,970 B2
(45) Date of Patent: Jul. 19, 2016

(54) BIOTELEMETRY SYSTEM

(75) Inventor: Mark Vastola, Lebanon, TN (US)

(73) Assignee: Wristdocs LLC, Lebanon, TN (US)

( * ) Notice: Subject to any disclaimer, the term of this patent is extended or adjusted under 35 U.S.C. 154(b) by 210 days.

(21) Appl. No.: 14/238,005

(22) PCT Filed: Aug. 8, 2012

(86) PCT No.: PCT/US2012/049896
§ 371 (c)(1),
(2), (4) Date: Apr. 11, 2014

(87) PCT Pub. No.: WO2013/022911
PCT Pub. Date: Feb. 14, 2013

(65) Prior Publication Data
US 2014/0296670 A1  Oct. 2, 2014

Related U.S. Application Data

(60) Provisional application No. 61/521,991, filed on Aug. 10, 2011, provisional application No. 61/602,363, filed on Feb. 23, 2012.

(51) Int. Cl.
*A61B 5/1455* (2006.01)
*A61B 5/00* (2006.01)
*A61B 5/01* (2006.01)
*A61B 5/021* (2006.01)
(Continued)

(52) U.S. Cl.
CPC ......... *A61B 5/14552* (2013.01); *A61B 5/14551* (2013.01); *A61B 5/6824* (2013.01); *A61B 5/01* (2013.01); *A61B 5/021* (2013.01); *A61B 5/02438* (2013.01); *A61B 5/08* (2013.01)

(58) Field of Classification Search
CPC .............. A61B 5/0059; A61B 5/1455; A61B 5/14551; A61B 5/14552; A61B 5/68; A61B 5/6801; A61B 5/6802; A61B 5/681; A61B 5/6824
See application file for complete search history.

(56) References Cited

U.S. PATENT DOCUMENTS

| | | | |
|---|---|---|---|
| 5,090,410 A * | 2/1992 | Saper | A61B 5/14552 600/310 |
| 6,253,098 B1 * | 6/2001 | Walker | A61B 5/1459 600/310 |
| 6,622,034 B1 * | 9/2003 | Gorski | A61B 5/14552 600/310 |

(Continued)

FOREIGN PATENT DOCUMENTS

| | | |
|---|---|---|
| EP | 0357249 | 3/1990 |
| EP | 0992214 | 12/2003 |

(Continued)

OTHER PUBLICATIONS

International Search Report and Written Opinion for PCT/US2013/074528 dated Feb. 14, 2014.
(Continued)

*Primary Examiner* — Eric Winakur
(74) *Attorney, Agent, or Firm* — DT Ward, PC; Donna T. Ward; Christopher P. Sullivan (57) ABSTRACT

The invention provides a biotelemetry system for disposition on the wrist. The device of the invention may be portable, untethered and in some instances, disposable. The features of the wrist biotelemetry system make it effective in stable, chronic or emergency medical settings.

14 Claims, 5 Drawing Sheets

(51) Int. Cl.
*A61B 5/024* (2006.01)
*A61B 5/08* (2006.01)

(56) References Cited

U.S. PATENT DOCUMENTS

| | | | |
|---|---|---|---|
| 6,637,434 | B2 | 10/2003 | Noble |
| 6,694,160 | B2 | 2/2004 | Chin |
| 7,190,986 | B1 | 3/2007 | Hannula et al. |
| 7,844,315 | B2 | 11/2010 | Al-Ali |
| 8,483,790 | B2 | 7/2013 | Hannula et al. |
| 2002/0077558 | A1 | 6/2002 | Itonaga et al. |
| 2006/0276702 | A1 | 12/2006 | McGinnis |
| 2009/0054751 | A1 | 2/2009 | Babashan et al. |
| 2011/0031289 | A1 | 2/2011 | Haskell et al. |
| 2012/0165630 | A1 | 6/2012 | Knight et al. |
| 2013/0079609 | A1 | 3/2013 | Besko |
| 2013/0104288 | A1* | 5/2013 | Schlottau ............. A61B 5/1455 2/209.13 |

FOREIGN PATENT DOCUMENTS

| | | |
|---|---|---|
| WO | 2005/023097 | 3/2005 |
| WO | 2006/123098 | 12/2005 |
| WO | 2006/005169 | 1/2006 |
| WO | 2013/030744 | 3/2013 |

OTHER PUBLICATIONS

Everett, J.S. et al., 2012. Making sense of skin color in clinical care. Clin Nurs Res. 21(4):495-516.

International Search Report for International Application No. PCT/US2012/049896 dated Nov. 5, 2012.

\* cited by examiner

BIOTELEMETRY SYSTEM

CROSS REFERENCE TO RELATED APPLICATIONS

This application is a 35 U.S.C. §371 U.S. National Phase Entry of International Application No. PCT/US2012/049896 filed on Aug, 8, 2012, which claims the benefit of U.S. Provisional Patent Application No. 61/521,991, filed Aug. 10, 2011, entitled "BIOTELEMETRY SYSTEM" and U.S. Provisional Patent Application No. 61/602,363, filed Feb. 23, 2012, entitled "BIOTELEMETRY SYSTEM", the contents of which are incorporated by reference in their entirety.

FIELD OF THE INVENTION

The present invention provides a portable, disposable biotelemetry system, including one or more sensors, capable of being mounted on one or more extremities, particularly the wrist.

BACKGROUND OF THE INVENTION

Biotelemetry is the process of measuring any one or more of a biometric. Telemetry systems in the art have traditionally been focused on the multi-measurement and monitoring of biological statistics yet have been tethered to large monitoring systems. The present invention provides a biotelemetry system focused on improvement at the "point of care" including improvements in portability, functionality and efficiency.

SUMMARY OF THE INVENTION

The present invention provides a biotelemetry device operative at, and/or which may be worn around, an extremity such as the wrist. In one embodiment, the system is a pulse oximetry system.

A pulse oximeter is a non-invasive medical device for measuring oxygenation of the blood. Oximetry involves the use of two light sources having differing wavelengths (usually red at 660 nm and infrared at 940 nm). The lights are sequentially passed through the patient's body or a portion of a patient's body to a photodetector. The changing absorbance of each of the two wavelengths is measured, allowing determination of the net absorbance as altered by the pulse of arterial blood. The ratio of absorbance between the red and infrared light caused by the variance between oxygenated and un-oxygenated blood (or hemoglobin status) is an indirect measure of the percent of hemoglobin molecules bound with oxygen molecules.

A majority of pulse oximeters currently available on the market suffer from lack of a secure fit being primarily attached via a clip to the fingertip. Alternative sensor placement is possible and has been reported for the toe, nose, forehead and ball of the foot. Wrist oximeters in the art, however, are still limited to the display module worn on the wrist like a wristwatch but with the sensor still placed on the tip of the finger and tethered to the wrist band display. Placement of the sensor on the wrist directly without any tethered component would improve the function and utility of the device.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

The present invention will be described, by way of example only, with reference to the accompanying Figures, in which:

FIG. 2A shows the sensor associated with the banding mechanism and the presence of a lengthwise strut to facilitate attachment to the wrist. FIG. 2B shows the same view with optional fastening mechanism. FIG. 2C shows the banding mechanism separate from the sensor to illustrate the presence of a window or pocket used to house the sensor.

FIG. 3 represents a three dimensional view of one embodiment of the biotelemetry system of the invention.

DETAILED DESCRIPTION

The present invention provides a portable biotelemetry system. The biotelemetry system of the present invention may be used with subjects of all ages from infants, including premature infants, through the elderly. In one embodiment, the system is unique in that the biotelemetry system may be disposed at a subject's extremity such as, but not limited to, the arm, the leg, the foot, the hand, the finger, the ankle and wrist and/or may be disposed on the patient's forehead area, torso and/or neck. For example, the system may be disposed on the subject's foot so that the ball of the foot is covered by the system. The system may comprise features which help in the subject's comfort, mobility, and ease of use such as, but not limited to, hypoallergenic materials, flexible materials, size and shape options of the system, and the ability for the system to expand due to swelling.

The system may further comprise features of being optionally wireless, disposable and modular. The biotelemetry system of the present invention may be wireless (portable) and may be battery supported. Where a battery is employed it is advantageous for the system to operate for long periods of time. Batteries may be chosen which provide basic functionality for at least 24, 28, or 72 hours or for at least 1, 2, 5, 7, or up to 14 days. When data from the system are sent to a monitor, the reports produced may have the capability of producing graphs of prolonged data streams or instant readouts. Telemetry monitors and graphing devices are well known in the art and can be used in conjunction with the biotelemetry system of the present invention. Such monitors include, but are not limited to, those which are tethered either with a cord or with wireless means to the sensor.

The biotelemetry system of the present invention has multiple uses in healthcare such as, but not limited to, in the development of an inpatient monitoring system, an outpatient monitoring system, and a fitness center monitoring system. Non-limiting examples of uses for inpatient monitoring include hospitals such as pediatric hospitals, assisted living facilities, nursing homes, rehabilitation facilities, intensive care units, respiratory departments, cardiac care centers, emergency departments and other specialized areas in medical facilities. Examples of outpatient monitoring include, but are not limited to, outpatient clinics, sleep centers, and rehabilitation facilities. In a further embodiment, the biotelemetry system of the present invention may be manufactured to be worn by a subject for extended periods of time such as, but not limited to, more than 1 day, more than 3 days, more than 5 days, more than 1 week, more than 2 weeks, more than a month, more than 3 months, more than 6 months, and more than 1 year. The system may also be employed in the field in settings such as for example in military applications where soldiers are often separated from direct healthcare providers. In this situation, the portable modular nature of the device allows for inclusion of the biotelemetry system in a standard first aid kit and may be easy enough to employ that any lay person can immediately attach the banding mechanism to an injured person and activate the sensor.

The present biotelemetry system may also be capable of providing information directly to the subject or to a user in the vicinity of the subject. The subject or the user may trigger the system to gather or provide information on the subject at a particular instance. In this case, the subject or the user would have access to an identifier button on the device that can be pushed to log a specific instance such as, but not limited to, when the subject feels short of breath, lightheaded, or weak. When the identifier button is pushed, information such as, but not limited to, the subject's vital statistics, the date and the time may also be recorded so that the information can be assessed to determine if there was a change in health status.

In one embodiment, the biotelemetry system functions as a pulse oximeter. Such a system including one or more sensors and associated banding mechanism are shown in FIGS. 1-5.

In FIG. 1A, the pulse oximeter sensor 200 is shown from a top view. The sensor 200 comprises an outer edge 201, a sensor cover or frame 202, a sensor window 203 positioned to allow light from the light emitting source to pass through and to be detected by the photodetector. The sensor cover or frame 202 may be manufactured of a pliable plastic or a polymer sheet, film or shaped article. As used herein, "pliable" means being able to bend freely and repeatedly without breaking Examples of pliable plastics include, but are not limited to, plastics which are above their glass transition temperature at room temperature. Examples of plastics include, but are not limited to, polyethylene, polypropylene, polystyrene, polyester, polycarbonate, polyvinylchloride, nylon, poly(methyl methacrylate) and the like. The pliable plastic or polymer sheet, film or shaped article may be colored with at least one color, may be biodegradable and/or may be superabsorbent. As used herein, "biodegradable" refers to a product which can be easily broken down into innocuous products.

The sensor 200 may range in size from about 1 mm to about 10 cm in length and be between about 1 mm to about 10 cm in width. In one embodiment, the length of the sensor may be from about 5 mm to about 1 cm, from about 10 mm to about 1 cm, from about 15 mm to about 1 cm, from about 20 mm to about 1 cm, from about 25 mm to about 1 cm, from about 30 mm to about 1 cm, from about 35 mm to about 1 cm, from about 40 mm to about 1 cm, from about 45 mm to about 1 cm, from about 50 mm to about 1 cm, from about 55 mm to about 1 cm, from about 60 mm to about 1 cm, from about 65 mm to about 1 cm, from about 70 mm to about 1 cm, from about 75 mm to about 1 cm, from about 80 mm to about 1 cm, from about 85 mm to about 1 cm, from about 90 mm to about 1 cm, from about 95 mm to about 1 cm, from about 0.5 cm to about 5 cm, from about 1 cm to about 5 cm, from about 1.5 cm to about 5 cm, from about 2 cm to about 5 cm, from about 2.5 cm to about 5 cm, from about 3 cm to about 5 cm, from about 3.5 cm to about 5 cm, from about 4 cm to about 5 cm, from about 4.5 cm to about 5 cm, from about 1 cm to about 10 cm, from about 2 cm to about 10 cm, from about 3 cm to about 10 cm, from about 4 cm to about 10 cm, from about 5 cm to about 10 cm, from about 6 cm to about 10 cm, from about 7 cm to about 10 cm, from about 8 cm to about 10 cm or from about 9 cm to about 10 cm. In one embodiment, the width of the sensor may be from about 5 mm to about 1 cm, from about 10 mm to about 1 cm, from about 15 mm to about 1 cm, from about 20 mm to about 1 cm, from about 25 mm to about 1 cm, from about 30 mm to about 1 cm, from about 35 mm to about 1 cm, from about 40 mm to about 1 cm, from about 45 mm to about 1 cm, from about 50 mm to about 1 cm, from about 55 mm to about 1 cm, from about 60 mm to about 1 cm, from about 65 mm to about 1 cm, from about 70 mm to about 1 cm, from about 75 mm to about 1 cm, from about 80 mm to about 1 cm, from about 85 mm to about 1 cm, from about 90 mm to about 1 cm, from about 95 mm to about 1 cm, from about 0.5 cm to about 5 cm, from about 1 cm to about 5 cm, from about 1.5 cm to about 5 cm, from about 2 cm to about 5 cm, from about 2.5 cm to about 5 cm, from about 3 cm to about 5 cm, from about 3.5 cm to about 5 cm, from about 4 cm to about 5 cm, from about 4.5 cm to about 5 cm, from about 1 cm to about 10 cm, from about 2 cm to about 10 cm, from about 3 cm to about 10 cm, from about 4 cm to about 10 cm, from about 5 cm to about 10 cm, from about 6 cm to about 10 cm, from about 7 cm to about 10 cm, from about 8 cm to about 10 cm or from about 9 cm to about 10 cm. In total the sensor thickness may range from about ½ mm to about 3 cm thick including the substrate and sensor cover. In one embodiment, the thickness of the sensor may be from about 0.5 mm to about 20 mm, from about 1 mm to about 20 mm, from about 1.5 mm to about 20 mm, from about 2 mm to about 20 mm, from about 2.5 mm to about 20 mm, from about 3 mm to about 20 mm, from about 3.5 mm to about 20 mm, from about 4 mm to about 20 mm, from about 4.5 mm to about 20 mm, from about 5 mm to about 20 mm, from about 5.5 mm to about 20 mm, from about 6 mm to about 20 mm, from about 6.5 mm to about 20 mm, from about 7 mm to about 20 mm, from about 7.5 mm to about 20 mm, from about 8 mm to about 20 mm, from about 8.5 mm to about 20 mm, from about 9 mm to about 20 mm, from about 9.5 mm to about 20 mm, from about 10 mm to about 20 mm, from about 10.5 mm to about 20 mm, from about 11 mm to about 20 mm, from about 11.5 mm to about 20 mm, from about 12 mm to about 20 mm, from about 12.5 mm to about 20 mm, from about 13 mm to about 20 mm, from about 13.5 mm to about 20 mm, from about 14 mm to about 20 mm, from about 14.5 mm to about 20 mm, from about 15 mm to about 20 mm, from about 15.5 mm to about 20 mm, from about 16 mm to about 20 mm, from about 16.5 mm to about 20 mm, from about 17 mm to about 20 mm, from about 17.5 mm to about 20 mm, from about 18 mm to about 20 mm, from about 18.5 mm to about 20 mm, from about 19 mm to about 20 mm, from about 19.5 mm to about 20 mm, from about 5 mm to about 1 cm, from about 10 mm to about 1 cm, from about 15 mm to about 1 cm, from about 20 mm to about 1 cm, from about 25 mm to about 1 cm, from about 30 mm to about 1 cm, from about 35 mm to about 1 cm, from about 40 mm to about 1 cm, from about 45 mm to about 1 cm, from about 50 mm to about 1 cm, from about 55 mm to about 1 cm, from about 60 mm to about 1 cm, from about 65 mm to about 1 cm, from about 70 mm to about 1 cm, from about 75 mm to about 1 cm, from about 80 mm to about 1 cm, from about 85 mm to about 1 cm, from about 90 mm to about 1 cm, from about 95 mm to about 1 cm, from about 0.5 cm to about 3 cm, from about 1 cm to about 3 cm, from about 1.5 cm to about 3 cm, from about 2 cm to about 3 cm or from about 2.5 cm to about 3 cm. The sensor may be configured to measure any number of vital statistics of the individual including, but not limited to, pulse oximetry, temperature, heart rate, respiration and blood pressure. In one embodiment, the sensor is a pulse oximetry sensor or pulse oximetry device (POD). In a further embodiment, the sensor provides a means of signal compensation of nitrous oxide ($N_2O$). Such compensation may be useful for measurement of oximetry output for persons undergoing anesthesia.

Depending on the intended use, the biotelemetry system may be configured to record, save, and upload historical data for clinical studies and patient information documentation. The system may be employed passively to measure vital statistics over a period of time or may be triggered by an event or situation which captures one or more metrics for storage or relay to a remote location. In this manner, the condition of a patient may be monitored for gradual or instant changes in biometrics which can signal to the patient or to a healthcare provider that one or more treatment regimens are needed.

The sensor itself may be made of adhesive or non-adhesive materials such as those described in U.S. Pat. No. 7,190,986, the contents of which are incorporated herein by reference in their entirety.

In one embodiment, the sensor and banding mechanism are modular with the sensor or multiple sensors being inserted into the banding mechanism as needed by a user such as, but not limited to, a healthcare professional. In another embodiment, inactivating tabs which separate operationally linked components are installed to prevent the system from engaging or becoming operational until desired. In the pulse oximeter embodiment, tabs may be placed such that the light emission or detection is covered until the sensor or sensors are in place in the banding mechanism and are needed by the health care professional. Inactivating tabs may also be placed to separate the battery power from the sensor. In this manner the biotelemetry system may be protected in less than hospital like settings until intentionally activated upon need.

The modular nature of separating the sensor from the banding mechanism affords the health care professional the option of reusing (not removing) the banding mechanism should a new sensor be needed. The old sensor may simply be removed and a new one put in its place. This aspect of the invention also aids in the reduction of nosocomial infections and the spread of germs in less than sterile conditions.

The sensor window may comprise the entire sensor cover or frame or may be a subportion thereof or multiple subportions thereof. It may extend the full length of the sensor 200 (as shown) or may only cover a central or at least one off central position on the sensor. The sensor window may be made of any material with sufficient transparency for light being utilized to pass through. Many plastics in the art have this property and will be known to one of skill such as, but not limited to, polyurethane. The sensor, if rotated around a longitudinal axis 200A by 90 degrees produces the view in FIG. 1B. In one embodiment the sensor may be chosen from the character and parameter requirements set by the monitor manufacturer. As a non-limiting example, a NELLCOR™ (Covidien-Nellcor, Boulder, Colo.) monitor may be used with photo optic sensor such as, but not limited to, an ELM series high precision LED sensor (Measurement Specialties™, Hampton, Va.) may be chosen for use in the present invention.

Shown in FIG. 1B are the substrate 205 adapted to receive or support the light emitting source 225 and its housing 220 and the photodetector 235 and its housing 230. A source-detector connection 260 between the source 225 and detector 235 are shown as a linear connection but can be in any shape or of any material which facilitates signal transmission between the two.

Both light emitting sources and photodetectors are well known in the art and may be selected to fit the size of the substrate selected.

Figure 5:
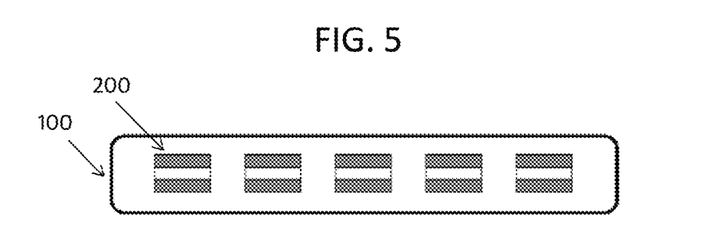
FIG. 5 represents an embodiment of the biotelemetry system of the invention having multiple sensors positioned radially about the banding mechanism.

In one embodiment, multiple sensors 200 can be positioned along the banding mechanism as shown in FIG. 5. Placement of the sensors along the banding mechanism may include radial positioning, even distribution, in-line positioning, side-by-side positioning, staggered positioning, zigzag positioning, serpentine positioning and random positioning. In another embodiment, modular sensors may be placed at locations that optimize the signal output. The signals from the multiple sensors may be amplified, filtered and averaged to give an equivalent output signal as a single sensor. Multiple sensors may be configured to provide parallel signaling or independent signaling. As used herein "multiple sensors" includes 2, 3, 4, 5, 6, 7, 8, 9 or more sensors.

A connection 280 between a sensor and an external monitor or signal processing unit is also shown. The connection 280 may be attached to the photodetector housing 230 at an angle selected from 90°, less than 90° and greater than 90° in the same plane as the photodetector housing. In another embodiment, the connection 280 may be attached to the photodetector housing 230 at an angle selected from 90°, less than 90° and greater than 90° from vertical. In order to improve patient comfort and mobility the attachment of the connection 280 to the photodetector housing 230 may further be flexible. The connection 280 may also be attached to the photodetector housing 230 using a shaped connector, such as, but not limited to, an "L" shaped connector. The shaped connector may further be flexible or rigid for improved patient comfort, fit and mobility. Neither the monitor nor signal processing unit is shown but may be selected from monitors and/or signals known in the art. Signal processing of the biotelemetry system may be performed within the sensor or the sensor may be tethered to a monitor.

In one embodiment, the light emitting source may be positioned or trained within its housing to emit light along an angled path. Such angle is shown in FIG. 1B and represented by the symbol, $\phi$. The angle of emitted light will be from 0-45 degrees from the vertical. This positioning affords the broadest sweep as the banding mechanism is wrapped around the curvature of the extremity such as, but not limited to, the wrist or the forehead, neck and torso. The limit on the angle ensures that light is not emitted which is not useable due to its inability to pass through the longer cross section of the extremity, forehead, neck and torso.

Figure 1:
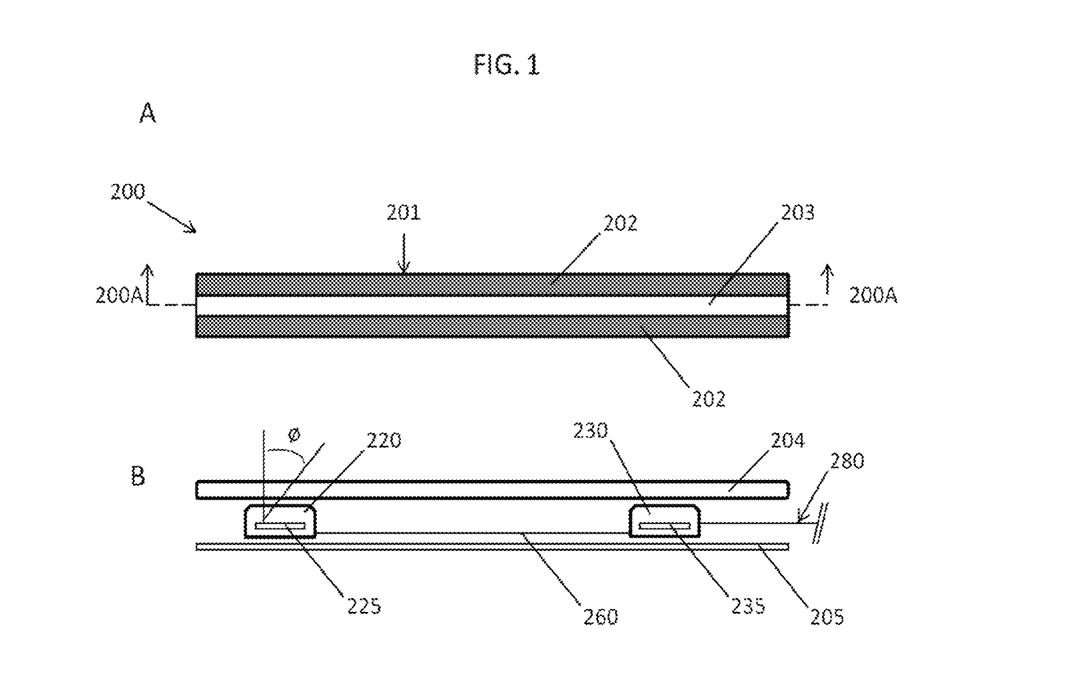
FIG. 1 represents a top (A) and cross section (B) view of the pulse oximeter sensor 200 of the present invention.
Figure 2:
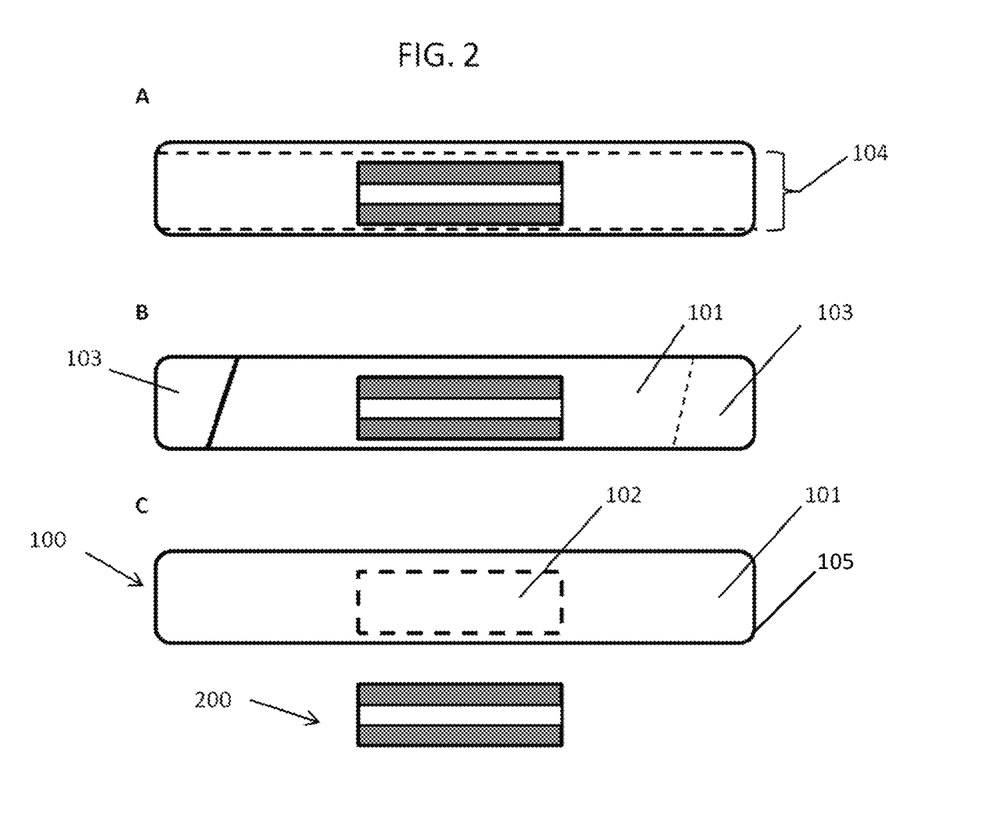
FIG. 2 represents three top views of the pulse oximeter sensor 200 of the present invention in various configurations with the banding mechanism 100.
Figure 3A:
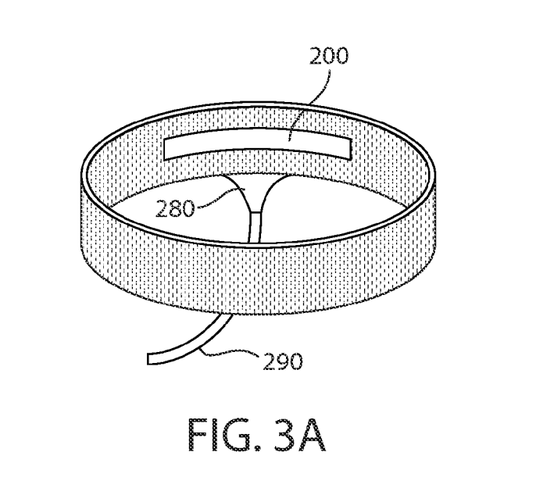
FIG. 3A shows the system with a continuous banding mechanism having an optional tethered signal cord from the sensor.
Figure 3B:
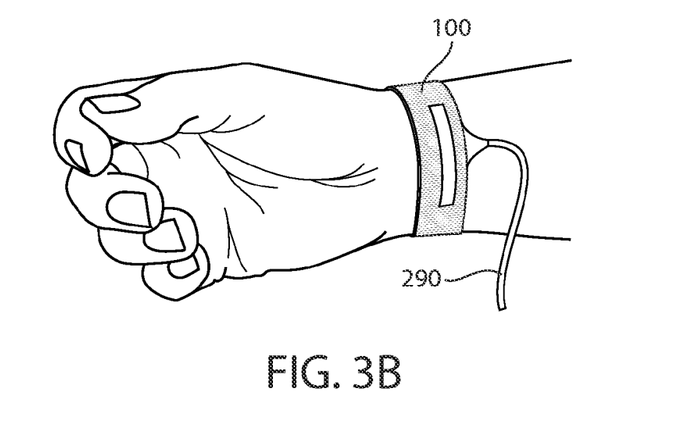
FIG. 3B shows the system of FIG. 3A on the wrist with the sensor being placed on the underside of the wrist.

FIG. 2 illustrates the banding mechanisms 100 or device of the invention. The skin contacting surface 101 is shown. FIG. 2A shows the sensor associated with the banding mechanism and the presence of a lengthwise strut 104 to facilitate attachment to the wrist. FIG. 2B shows the same view with an optional means of fastening 103 at the terminal ends of the banding mechanism. Such means of fastening may be any known in the art including, but not limited to, Velcro, adhesive, static, fasteners, snaps, buttons, clips, slotted grooves, magnetic, buckle and combinations thereof. The means of fastening utilized with the invention may be easily removed or they may be secured to ensure the device remains on the subject. FIG. 2C shows the banding mechanism 100 separate from the sensor 200 to illustrate the presence of a window area 102 which may further include a pocket to house the sensor. The window area or pocket may be integral to the banding mechanism or may be modular such that as a pocket it may be attached to the banding mechanism in any position along it by any means of attachment. In a further embodiment, the invention includes more than one window or pocket 102 which may house more than one sensor, or house the sensor in more than one location on the banding mechanism.

The biotelemetry system includes a means for banding the device to the body. The means for banding may be a banding mechanism 100 manufactured from any material that is flexible such as paper, plastic, metal, metal coated plastic, fabric, pocketed strut or combinations thereof. The banding mechanism may further be manufactured using hypoallergenic material. As used herein, "hypoallergenic" refers to material unlikely to cause an allergic reaction. In one embodiment, the banding mechanism may be a wrist band or sweat band like material. This banding mechanism may be manufactured from an elastic, a combination of fabric and elastic or stretching fabric. In one embodiment, the banding mechanism may be manufactured to allow for changes in the circumference of the subject's extremity due to swelling and/or growth and to provide a more comfortable fit for the subject. In one embodiment, the outer edge of the banding mechanism 105 may be, but is not limited to, straight, curved, zigzag, decorative and the like. As used herein "decorative" refers to a wide range of patterns such as, but not limited to, gentle curves, scallops, deeply jagged edges and the like.

FIG. 3 illustrates a continuous banding mechanism 100. Shown in the figure is the sensor 200 as seen through the window area 102, as well as the connection 280 to a tethered signal cord 290. The window area 102 may include at least one display window to allow for light to be transmitted from the sensor to the subject's extremity. In one embodiment, the window area 102 may include at least two display windows which may be aligned in parallel or not parallel. The shape of the display windows may be, but is not limited to, circular, square, rectangular, triangular, polygonal, concave polygon, constructible polygon, convex polygon, cyclic polygon, equiangular polygon, equilateral polygon, regular polygon, henagon, digon, quadrilateral, cyclic quadrilateral, kite, parallelogram, equilateral parallelogram, rhomboid, tangential quadrilateral, trapezoid or trapezium, isosceles trapezoid, pentagon, regular pentagon, hexagon, heptagon, octagon, regular octagon, nonagon, decagon, regular decagon, hendecagon, dodecagon, hexadecagon, icosagon, star without crossing lines, star polygon, hexagram, heptagram, octagram, decagram, pentagram, annulus, arbelos, disc, crescent, elliptical, oval, and semicirclular. In one embodiment, the sensor or sensors may be tethered to a monitor using a wireless LAN (Wi-Fi), Bluetooth, or by physical connection using a tethered signal cord 290. In one embodiment, a tethered signal cord 290 is used where the tether may include a mechanism to be able to swap out leads and connectors to allow the biotelemetry system to interface with multiple monitors. In a further embodiment, the tether signal cord 290 may include at least one custom lead and/or connector which may be able to connect to a specific monitor with the compatible custom port. As a non-limiting example, the tether signal cord 290 may include a USB port which may connect to an adaptor allowing for the tether to be connected to a variety of ports such as, but not limited to, a serial port, a parallel port, a USB port and an Ethernet port. The length of the tether signal cord 290 for the biotelemetry system may be greater than 0.1 m, greater than 1 m, greater than 3 m, or greater than 5 m. In one embodiment, the tether signal cord 290 may be about 1 m to about 5 m in length.

Figure 4A:
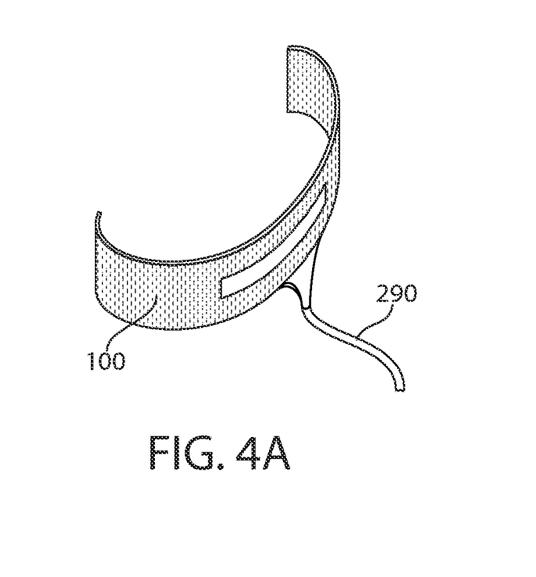
FIG. 4 represents a three dimensional view of one embodiment of the biotelemetry system of the invention having an opened banding mechanism and an optional tethered signal cord from the sensor.
Figure 4B:
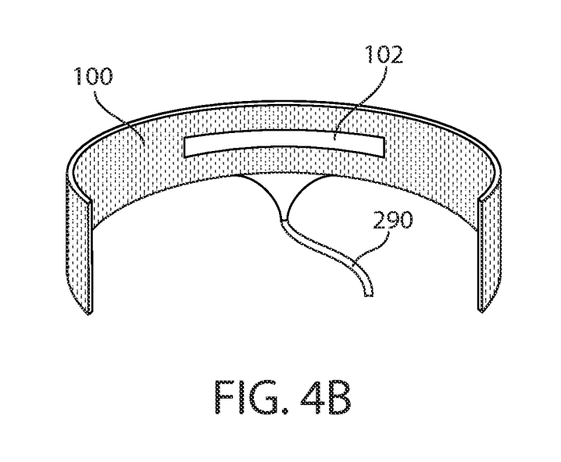

In one embodiment, the banding mechanism is a pocketed strut and comprises a lengthwise strut enveloped in a plastic pocket whereby providing a bending pressure to the banding mechanism results in the coiling of the strut and ligature of the sensor or sensors around the wrist. Such an open banding mechanism is shown in FIG. 4. Shown in FIG. 4 is an open banding mechanism with a tethered signal cord 290. The sensor may be viewed through the window area 102.

It is to be understood that the words which have been used are words of description rather than limitation, and that changes may be made within the purview of the appended claims without departing from the true scope and spirit of the invention in its broader aspects.

While various embodiments of the invention have been particularly shown and described, it will be understood by those skilled in the art that various changes in form and details may be made therein without departing from the spirit and scope of the invention as defined by the appended claims.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

What is claimed is:

1. A device comprising;
   (a) two or more disposable pulse oximeter sensor modules, each comprising;
      (i) a light emitting source, wherein said light emitting source is capable of sequentially emitting a red light with a wavelength of about 660 nm and an infrared light with a wavelength of about 940 nm;
      (ii) a photodetector spaced apart from said light emitting source and capable of detecting reflected light from said light emitting source;
      (iii) a substrate adapted to support said light emitting source and said photodetector, said substrate comprising a molded plastic template;
      (iv) a source-detector connection connecting said light emitting source to said photodetector; and
      (v) a sensor cover having an integral sensor window, wherein said sensor cover is positioned to retain said light emitting source, said photodetector, and said source-detector connection between said sensor cover and said substrate; and wherein said sensor window is positioned to allow light from said light emitting source to pass through and to be detected by said photodetector;
   (b) a banding mechanism, wherein said banding mechanism is configured to be worn around the wrist, and wherein the banding mechanism is capable of circumscribing the wrist, said banding mechanism having:
      a skin contacting surface, said skin contacting surface capable of maintaining contact with at least 50% of the wrist skin surface; and
      an integral pocket configured to receive said two or more disposable pulse oximeter sensor modules;
   (c) a strut enveloped lengthwise within said banding mechanism, wherein the strut is configured such that providing a bending pressure to the banding mechanism results in the coiling of the strut and ligature of the banding mechanism around the wrist;
   (d) a window area on the skin contacting surface of said banding mechanism, wherein said window area comprises a pliable plastic sheet, and wherein said window area is integrated into said integral pocket and disposed to allow light to enter and exit the inner area of said integral pocket; and (e) a signal processing unit, wherein said signal processing unit is capable of receiving one or more signal from said photodetector and wherein said signal processing unit determines the percent of hemoglobin molecules bound with oxygen molecules by determining the ratio of absorbance between said red light and said infrared light based on said one or more signal from said photodetector.

2. The device of claim 1 wherein the banding mechanism comprises a material selected from the group consisting of paper, plastic, metal, metal coated plastic, fabric, and combinations thereof.

3. The device of claim 2 wherein the banding mechanism material is a flexible material.

4. The device of claim 1 wherein placement of the two or more disposable pulse oximeter sensor modules along the banding mechanism is selected from the group consisting of radial positioning, even distribution, in-line positioning, side-by-side positioning, staggered positioning, zigzag positioning, serpentine positioning and random positioning.

5. The device of claim 1 wherein the one or more signal from at least two photodetectors are amplified, filtered and averaged by the signal processing unit.

6. The device of claim 1 further comprising an oximeter monitor connected directly to the signal processing unit, wherein said monitor contains at least one display window.

7. The device of claim 6 wherein the monitor contains two or more display windows.

8. The device of claim 6 wherein the at least one display window has a shape selected from the group consisting of circular, square, rectangular, triangular, polygonal, concave polygon, constructible polygon, convex polygon, cyclic polygon, equiangular polygon, equilateral polygon, regular polygon, henagon, digon, quadrilateral, cyclic quadrilateral, kite, parallelogram, equilateral parallelogram, rhomboid, tangential quadrilateral, trapezoid or trapezium, isosceles trapezoid, pentagon, regular pentagon, hexagon, heptagon, octagon, regular octagon, nonagon, decagon, regular decagon, hendecagon, dodecagon, hexadecagon, icosagon, star without crossing lines, star polygon, hexagram, heptagram, octagram, decagram, pentagram, annulus, arbelos, disc, crescent, elliptical, oval, and semicirclular.

9. The device of claim 8 wherein the at least one display window shape is circular.

10. The device of claim 1 wherein the dimensions of said two or more disposable pulse oximeter sensor modules are between about 1 mm to about 10 cm in length, between about 1 mm to about 10 cm in width and thickness between about ½ mm to about 3 cm including said substrate.

11. The device of claim 10 wherein the dimensions of said two or more disposable pulse oximeter sensor modules are between about 1 mm to about 5 cm in length, between about 3 mm to about 5 cm in width and thickness between about ½ mm to about 3 cm including said substrate.

12. The device of claim 10 wherein said two or more disposable pulse oximeter sensor modules are of a length selected from the group consisting of from about 5 mm to about 1 cm, from about 0.5 cm to about 5 cm, and from about 3 cm to about 10 cm.

13. The device of claim 10 wherein said two or more disposable pulse oximeter sensor modules are of a width selected from the group consisting of from about 5 mm to about 1 cm, from about 0.5 cm to about 5 cm, and from about 3 cm to about 10 cm.

14. The device of claim 10 wherein said two or more disposable pulse oximeter sensor modules are of a thickness selected from the group consisting of from about 0.5 mm to about 20 mm, from about 5 mm to about 1 cm and from about 0.5 cm to about 3 cm.

* * * * *